United States Patent
Karni

(10) Patent No.: US 10,342,616 B2
(45) Date of Patent: Jul. 9, 2019

(54) WINDOW FOR SURGICAL LASER

(71) Applicant: Alma Lasers Ltd., Caesarea (IL)

(72) Inventor: Ziv Karni, Kfar Shmaryahu (IL)

(73) Assignee: Alma Lasers Ltd.

( * ) Notice: Subject to any disclaimer, the term of this patent is extended or adjusted under 35 U.S.C. 154(b) by 87 days.

(21) Appl. No.: 15/491,528

(22) Filed: Apr. 19, 2017

(65) Prior Publication Data

US 2017/0296272 A1 Oct. 19, 2017

Related U.S. Application Data

(60) Provisional application No. 62/324,418, filed on Apr. 19, 2016.

(51) Int. Cl.
| | |
|---|---|
| *A61B 18/20* | (2006.01) |
| *A61B 1/00* | (2006.01) |
| *A61B 1/06* | (2006.01) |
| *A61N 5/06* | (2006.01) |
| *A61B 1/303* | (2006.01) |
| *A61B 90/30* | (2016.01) |
| *H01S 3/034* | (2006.01) |
| *H01S 3/223* | (2006.01) |
| *A61B 18/00* | (2006.01) |
| *A61N 5/067* | (2006.01) |

(52) U.S. Cl.
CPC .......... *A61B 18/20* (2013.01); *A61B 1/00135* (2013.01); *A61B 1/063* (2013.01); *A61B 1/303* (2013.01); *A61B 90/30* (2016.02); *A61N 5/0603* (2013.01); *H01S 3/034* (2013.01); *H01S 3/2232* (2013.01); *A61B 2018/005* (2013.01); *A61B 2018/00559* (2013.01); *A61B 2018/20553* (2017.05); *A61N 2005/067* (2013.01); *A61N 2005/0608* (2013.01); *A61N 2005/0611* (2013.01); *A61N 2005/0659* (2013.01)

(58) Field of Classification Search
CPC ......... A61B 18/20; A61B 90/30; H01S 3/034; H01S 3/2232
See application file for complete search history.

(56) References Cited

U.S. PATENT DOCUMENTS

| 8,187,481 | B1 | 5/2012 | Hobbs | |
|---|---|---|---|---|
| 2001/0001118 | A1 * | 5/2001 | Asah | A61B 18/203 |
| | | | | 606/9 |
| 2002/0045811 | A1 * | 4/2002 | Kittrell | A61B 1/00096 |
| | | | | 600/407 |
| 2011/0019174 | A1 | 1/2011 | Soer et al. | |

FOREIGN PATENT DOCUMENTS

WO    WO2016044212 A1    3/2016

OTHER PUBLICATIONS

PCT/IB17/52259, filed Apr. 19, 2017, like the present application, claims the benefit of U.S. Appl. No. 62/324,418. The ISR and IPRP (written opinion) dated Aug. 7, 2017. They are being submitted with this IDS. The ('Y') citations are listed above in this IDS.

* cited by examiner

*Primary Examiner* — Christian A Sevilla

(57) ABSTRACT

A laminated laser window having an inner layer transparent to light having wavelengths between 3.5 micrometers and 12 micrometers and having as an outer surface a nanometric-thick outer layer of $SiO_2$. The window allows the passage of light within this wavelength range, for example from a $CO_2$ laser. In The $SiO_2$ outer layer maintains biocompatibility when used in laser devices for insertion into externally accessible bodily cavities.

19 Claims, 2 Drawing Sheets

WINDOW FOR SURGICAL LASER

CROSS-REFERENCE TO RELATED APPLICATIONS

The present application takes priority from U.S. provisional patent application No. 62/324,418, filed 2016 May 4.

FIELD OF INVENTION

The present invention relates to a window component for a laser tool. Certain embodiments relate to a laser medical probe.

BACKGROUND OF INVENTION

The use of diamond as a window material in a laser tool for medical use is known. Diamond is useful as a window material as it has low absorption for infrared wavelengths in order to transmit a high power laser beam. However, diamond is expensive. Diamond windows are discussed in U.S. Pat. No. 9,040,131, which is hereby incorporated by reference.

Various less expensive alternatives have been tried for high transparency windows for lasers at mid-IR wavelengths (3.5-12 micron), particularly CO2 (10.6 micron). These include Ge, GaAs, CdTe, ZnSe, NaCl, and KCl. The window is often coated with AR/AR (internal and external anti-reflective coating).

ZnSe has been found to be the best of these window materials. However the use of these materials in medical applications, including surgery, has been limited as there are questions about biocompatibility.

SiO2 is a biocompatible compound. It has been used in laser windows for wavelengths from around 0.2 to 3.5 microns but has not been suitable for mid-IR wavelengths, due to its low transmissivity at those wavelengths.

A biocompatible coating for windows for mid-IR wavelength lasers has not been found that is easily applied and inexpensive.

SUMMARY OF INVENTION

The present invention is directed to a laminated laser window, comprising: an inner layer transparent to light having wavelengths between 3.5 micrometers and 12 micrometers; and constituting an outer surface of the window, a nanometric-thick outer layer of SiO2. The window is thereby configured to allow passage of light having said wavelengths therethrough.

In some embodiments, the outer layer of SiO2 is not more than 150 nm thick, is between 100 nm and 150 nm thick, or is less than 100 nm thick.

In some embodiments, the inner layer is at least one selected from the group comprising Ge, GeAs, CdTe, ZnSe, NaCl, KCl and ZnSe In some embodiments, the window allows passage of light having a wavelength of 10.6 micrometers.

In some embodiments, the window allows passage of light generated by a CO2 laser.

In some embodiments, the first layer is an innermost layer of the window.

In some embodiments, the there are no other layers except the first layer and the outer layer.

In some embodiments, there is intervening layer between the first layer and the outer layer.

In some embodiments, the intervening layer is an AR layer.

In some embodiments a medical device is provided for illumination of living tissue with light, the device body has a wall with an outer surface and a laser window as described earlier in this summary constituting at least a portion of the wall, thereby allowing light having said wavelengths to pass from inside said body to outside said body through said laser window.

In some embodiments, the outer layer of said laser window in the device is located to allow it to contact bodily tissue during use of the device.

In some embodiments the body of the device is for insertion into a bodily cavity, such as the vagina.

In some embodiments the device further comprises a CO2 laser.

In some embodiments the device body constitutes a sheath for a treatment device.

In some embodiments the a nanometric outer layer of SiO2 is used in a laser window for coating an inner layer, the inner layer transparent to light having wavelengths between 3.5 micrometers and 12 micrometers.

BRIEF DESCRIPTION OF THE DRAWINGS

The invention will now be described with reference to the drawings wherein.

REFERENCE NUMERALS IN THE DRAWINGS

| window | 14 | sheath | 6 |
| laser treatment head | 2 | laser beam | 4 |
| axis | 12 | deflector | 22 |
| inner layer | 23 | outer surface | 25 |
| body cavity | 27 | | |

DETAILED DESCRIPTION OF THE INVENTION

SiO2-based nano-coatings have been developed for glass and glazed ceramic. The non-stick coatings enable smooth, glass-like surfaces to have less contact with dirt particles. Coating characteristics include hydrophobicity, food safety (inert), and anti-stick properties. An example of such a coating is manufactured by Nano-Care Deutschland AG (see, http://www.nanocare-ag.com/glas_keramik/).

The present inventor has found that at nanoscale, SiO2 is substantially transmissive at mid-IR wavelengths.

He has further found that high transparency windows, particularly ZnSe, coated with nanoscale SiO2, can serve as biocompatible windows for medical lasers at mid-IR wavelengths.

Figure 1:
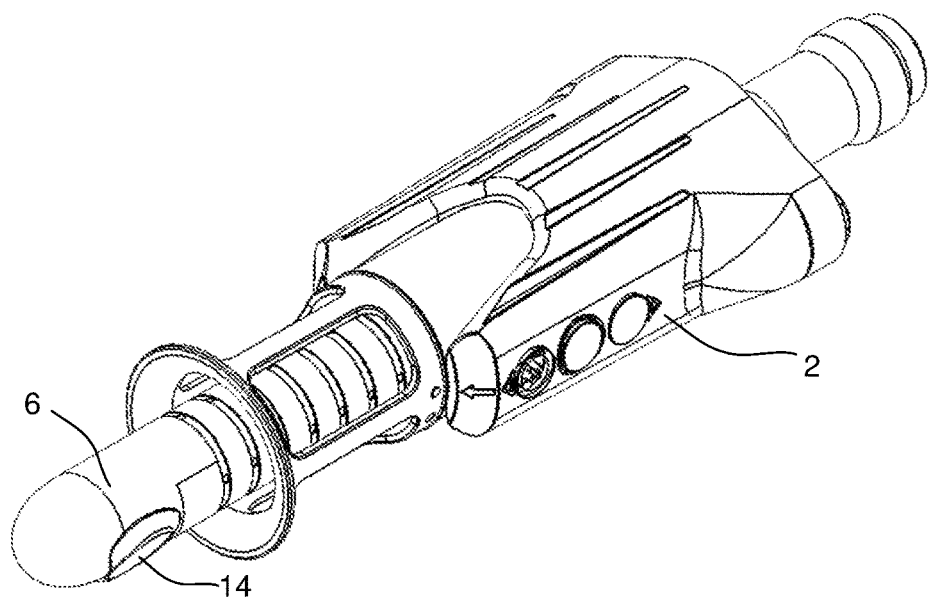
FIG. 1 is a perspective view of a laser treatment device comprising a laser window in accordance with an embodiment of the invention.

FIG. 1 shows an exemplary window 14 forming part of a biocompatible disposable sheath 6 fitted on a laser treatment head 2 for use in externally-accessible bodily cavities, such as the vagina or rectum. The laser treatment head is described in U.S. patent application Ser. No. 15/473,621, filed 2017 Mar. 30, which is hereby included by reference as if fully set-forth herein.

Window 14 comprises an inner layer 23 that is transparent to light having wavelengths between 3.5 micrometers and 12 micrometers. The external surface of the inner layer is coated by an outer layer 25 of nanometric SiO2.

In some embodiments, the inner layer 23 comprises ZnSe. In some embodiments, the inner layer 23 has an AR/AR coating, with the external AR coating lying between inner layer 23 and outer layer 25. Window 14 is substantially transmissive to a CO2 laser.

Figure 2:
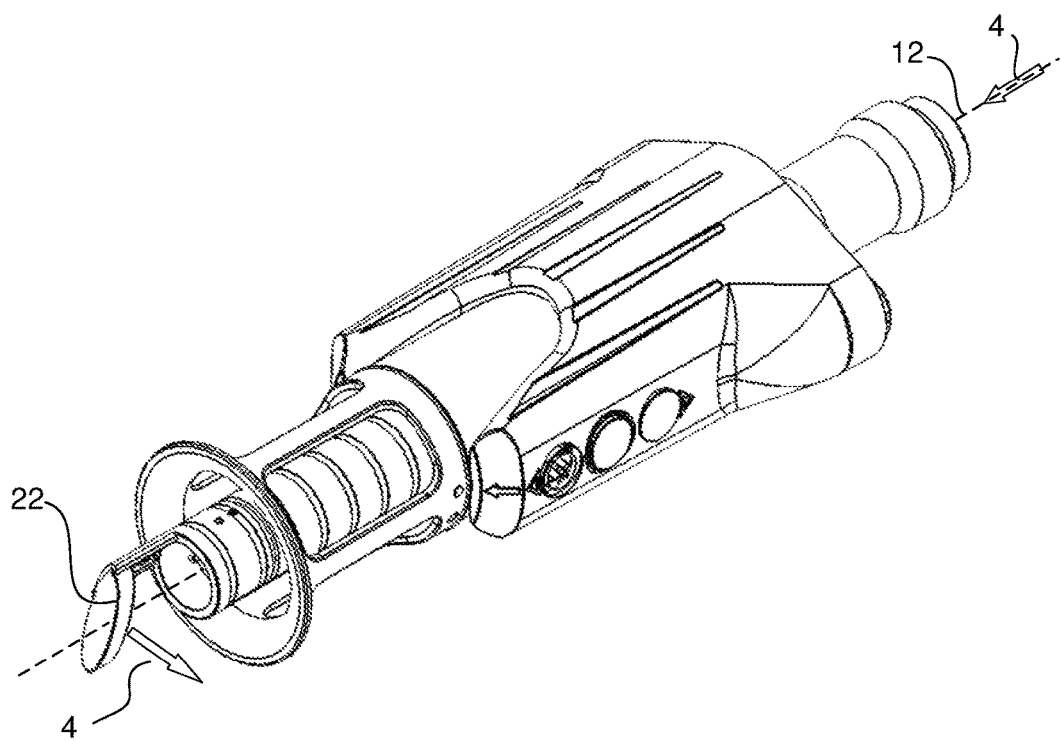
FIG. 2 is a perspective view of the device of FIG. 1 with the window removed.

FIG. 2 shows the laser treatment head 2 with the sheath removed.

Figure 3:
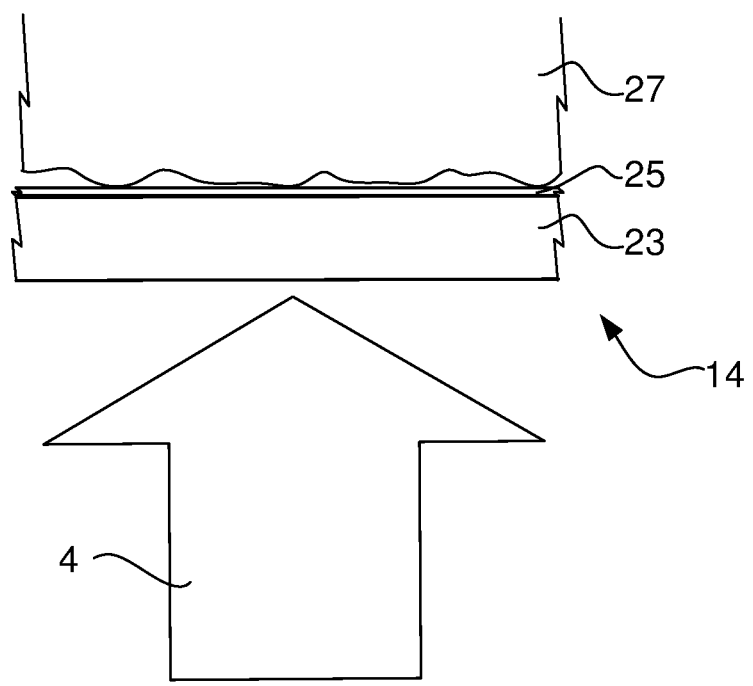
FIG. 3 is a cross sectional view of a section of the laser window inside a bodily cavity.

In use, laser treatment head 2 is inserted into an externally accessible bodily cavity. Laser beam 4 passing through laser treatment head 2 coaxially with linear axis 12 impinges on deflector 22 and is deflected laterally, away from laser treatment head 2, through window 14 to the wall 27 of the bodily cavity. FIG. 3 shows a cross sectional view of a portion of window 14 and of wall 27 of the bodily cavity.

The thickness of the SiO2 layer is less than 100 micron, preferably 100-150 nm.

The invention claimed is:

1. A laminated laser window, comprising:
   a. an inner layer transparent to light having wavelengths between 3.5 micrometers and 12 micrometers; and
   b. constituting an outer surface of the window, a nanometric-thick outer layer of SiO2 the window thereby configured to allow passage of light having said wavelengths therethrough.

2. The laser window of claim 1, wherein said outer layer of SiO2 is not more than 150 nm thick.

3. The laser window of claim 1, wherein said outer layer of SiO2 is between 100 nm and 150 nm thick.

4. The laser window of claim 1, wherein said outer layer of SiO2 is less than 100 nm thick.

5. The laser window of claim 1, wherein said inner layer is at least one selected from the group comprising Ge, GeAs, CdTe, ZnSe, NaCl, KCl and ZnSe.

6. The laser window of claim 5, wherein said inner layer is of ZnSe.

7. The laser window of claim 1, said window allowing passage of light having a wavelength of 10.6 micrometers.

8. The laser window of claim 1, said window allowing passage of light generated by a CO2 laser.

9. The laser window of claim 1, said first layer being an innermost layer of said window.

10. The laser window of claim 1, said window devoid of any layer except said first layer and said outer layer.

11. The laser window of claim 1, further comprising an intervening layer between said first layer and said outer layer.

12. The laser window of claim 11, wherein said intervening layer is an AR layer.

13. A medical device for illumination of living tissue with light, comprising:
   a body having a wall with an outer surface,
wherein a laser window of claim 1 constitutes at least a portion of said wall, thereby allowing light having said wavelengths to pass from inside said body to outside said body through said laser window.

14. The device of claim 13, wherein said outer layer of said laser window is located to allow contact of said outer layer of said window with bodily tissue during use of the device.

15. The device of claim 13, said body for insertion into a bodily cavity.

16. The device of claim 15, wherein said bodily cavity is a vagina.

17. The device of claim 13, further comprising a CO2 laser.

18. The device of claim 13, said body constituting a sheath for a treatment device.

19. Use of a nanometric outer layer of SiO2 in a laser window for coating an inner layer, the inner layer transparent to light having wavelengths between 3.5 micrometers and 12 micrometers.

* * * * *